United States Patent [19]
Domeier et al.

[11] Patent Number: 4,794,190
[45] Date of Patent: Dec. 27, 1988

[54] AROMATIC MALEIMIDE-ISOMALEIMIDE COMPOUND

[75] Inventors: Linda A. Domeier; Elke M. Clark, both of Flemington, N.J.

[73] Assignee: Amoco Corporation, Chicago, Ill.

[21] Appl. No.: 8,602

[22] Filed: Jan. 28, 1987

[51] Int. Cl.⁴ .......................................... C07D 207/244
[52] U.S. Cl. ..................... 548/548; 526/262; 548/407; 548/521; 549/507
[58] Field of Search .................... 548/548; 526/262; 549/507

[56] References Cited

U.S. PATENT DOCUMENTS 4,654,407 3/1987 Domeier .............................. 526/262

Primary Examiner—Harold D. Anderson
Attorney, Agent, or Firm—Richard J. Schlott; William H. Magidson; Ralph C. Medhurst

[57] ABSTRACT

Alpha-(4-maleimidophenyl)-alpha'-(4-isomaleimidophenyl) diisopropyl benzene, as a novel composition of matter. The compound, which may be used as a component of curable thermoset resins or as a unique, difunctional synthesis intermediate having non-symmetrical reactivity, may be prepared from the corresponding bis-maleamic acid by dehydrating at or below ordinary, ambient temperatures, using acetic anhydride or a similar dehydrating agent.

2 Claims, No Drawings

AROMATIC MALEIMIDE-ISOMALEIMIDE COMPOUND

CROSS-REFERENCE TO RELATED U.S. APPLICATIONS

This application is a continuation-in-part of U.S. application Ser. No. 761,432, filed Aug. 2, 1985, now U.S. Pat. No. 4,654,407.

BACKGROUND OF THE INVENTION

This invention relates in general to novel bismaleimide compositions. In one aspect, this invention relates to novel aromatic maleimide compounds such as alpha, alpha"-bis(4-maleimidophenyl)-meta-diisopropylbenzene and alpha, alpha'-bis(4-maleimidophenyl)-para-diisopropylbenzene, and to related maleimide-isomaleimide compounds. The invention further relates to the use of maleimide compositions as resin precursors.

Advanced composites are high strength, high modulus materials which are finding increasing use as structural components in aircraft, automotive, and sporting goods applications. Typically they comprise structural fibers such as carbon fibers in the form of woven cloth or continuous filaments embedded in a thermosetting resin matrix.

Most advanced composites are fabricated from pre-preg, a ready-to-mold sheet of reinforcement impregnated with uncured or partially cured resin. Resin systems containing an epoxide resin and aromatic amine hardener are often used in prepreg. However, most epoxy formulations absorb moisture which reduces their high temperature properties. As a result they are not suitable for use at 350° F. or greater in a moisture saturate condition.

Prepreg resins for use at 350° F. have been based on aromatic bismaleimides, often in combination with additional, usually liquid diluents which may contain other reactive groups such as amines, epoxides, cyanates or the like.

A variety of aromatic bismaleimides are presently available which comprise one, two or four aromatic rings in the structure. In the parent application U.S. Pat. No. 761,432, filed Aug. 2, 1985, the entire teachings of which are incorporated herein by reference, there is disclosed a group of bismaleimides containing three aromatic rings in the molecule. Bismaleimides containing one or two aromatic rings tend to give formulations which are characterized by high Tg, together with low toughness and high water absorption. Equivalent formulations in which the aromatic nucleus has four or more aromatic rings may have better water absorption and toughness properties, but exhibit low Tg values. However, as is disclosed in the parent application, novel bismaleimides containing three aromatic rings in the structure are useful in preparing matrix resin formulations with an improved balance of properties.

Also disclosed in the art, for example in U.S. Pat. No. 2,980,694, are aromatic isomaleimides, i.e., compounds having the structure:

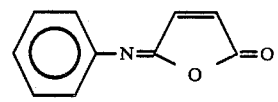

Although such compounds have been isolated, they generally are unstable and readily rearrange either thermally or chemically to the corresponding maleimide structure. For that reason, their preparation from the corresponding amide acids is usually accomplished using reaction conditions selected to avoid isomerizing the resulting isomaleimide structure.

SUMMARY OF THE INVENTION

The instant invention is a novel, difunctional compound having both isomaleimide and maleimide functionality and a method for its preparation. The novel maleimide-isomaleimide of this invention is readily isolated in the form of a stable, crystalline solid, and may be used as a synthesis intermediate and as a bis-imide precursor. The compound has particular utility as a synthesis intermediate by virtue of the recognized differences in reactivity for the two functionalities.

DETAILED DESCRIPTION OF THE INVENTION

The novel maleimide-isomaleimide compounds of this invention are those having the following structure:

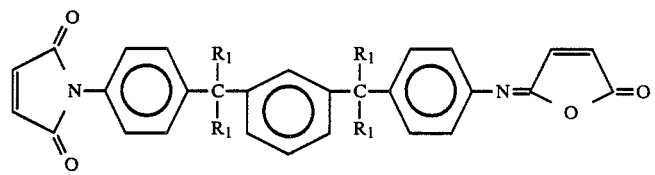

wherein Ar is an arylene radical and each $R_1$ is independently selected from the group consisting of H and $C_1$-$C_4$ alkyl. Particularly preferred is the compound having the structure:

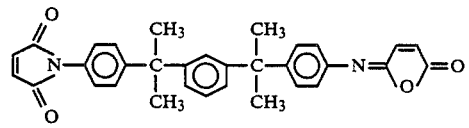

Bismaleimides are prepared by condensing aromatic diamines with maleic anhydride, substituted maleic anhydrides or an anhydride precursor under a variety of conditions. The initial products are generally the corresponding bis(amide-acids). These precursors are then cyclized in a subsequent step, usually by employing a dehydrating agent such as acetic anhydride or the like. Although the course of such cyclizing processes may involve the production of isoimides as fleeting intermediates, isoimides are not normally isolable from these reaction mixtures.

The novel aromatic maleimide-isomaleimide of this invention is produced, ordinarily in combination with the corresponding bismaleimide or bis(isomaleimide), when the starting diamine is alpha, alpha-bis(4-aminophenyl)-metadiisopropylbenzene. The yield of desired product will vary depending upon reaction conditions and may comprise from 5 wt % to as much as 95 wt % of the crude product mixture.

The diamines useful in the practice of this invention are generally available from commercial sources, and methods for preparing the diamines are also well known.

The practice of the invention will be better understood from a consideration of the following examples, which are provided by way of illustration and are not intended to be limiting.

EXAMPLE 1

Preparation of α, α'-Bis(4-maleimidophenyl)-meta-diisopropylbenzene

A 3 L 4-neck flask equipped with an overhead stirrer, a nitrogen gas dispersion tube and outlet, an addition funnel, and a thermometer with a temperature controller was charged with 444 ml acetone and 98.2 g maleic anhydride. The mixture was stirred to dissolve the maleic anhydride and sparged with nitrogen for 15 minutes. A solution of 150 g of α, α'bis(4-aminophenyl)-metadiisopropylbenzene in 444 ml acetone was added over 30 minutes during which time the reaction mixture formed an opaque, light yellow slurry. The slurry was stirred and heated at 40° C. for one hour.

The reaction mixture was then charged with 4.7 g of $MgCl_2 \cdot 6H_2O$, 23 ml triethylamine, and 238 g of acetic anhydride which was added over 15 minutes. Stirring and heating at 40° C. were continued for three hours and then the heat was turned off while stirring continued for 16 hours. About 20 minutes after the end of the acetic anhydride addition, the slurry changed to a clear gold solution which grew darker with time.

After diluting the reaction mixture with 600 ml of dichloromethane, it was washed (12 L separatory flask) with 5×1 L of 0.25M potassium carbonate, once with dilute brine, twice with water and again with brine. The methylene chloride solvent was then removed under vacuum and the residue was taken up in 4 L of acetone and then coagulated in 9 to 10 parts water per portion of acetone solution. The precipitate was collected and dried in an oven under vacuum. Over a period of two days the oven heat was gradually increased until the material formed a brittle melt (~70° C.).

The proton NMR was consistent with the expected bismaleimide structure. LC analysis showed one major product with two minor impurities.

COMPARATIVE EXAMPLE A

Preparation of α, α'-Bis(4-maleimidophenyl)para-diisopropylbenzene

A 5 L 4-neck flask equipped with an overhead stirrer, a nitrogen gas dispersion tube and outlet, and addition funnel, and a thermometer with a temperature controller was charged with 880 ml acetone and 166.7 g maleic anhydride. The mixture was stirred to dissolve the maleic anhydride and then sparged with nitrogen for 15 minutes. A solution of 250 g of α, α'-Bis(4-aminophenyl)-paradiisopropylbenzene in 1680 ml acetone was added ove 30 minutes during which time the reaction mixture formed an opaque yellow slurry. The slurry was stirred and heated at 40° C. for one hour.

The reaction was then charged with 8.03 g of $MgCl_2 \cdot 6H_2O$, 39 ml triethylamine, and 404 g of acetic anhydride which was added over 15 minutes. Stirring and heating at 40° C. were continued for about 20 hours during which time the slurry changed to green-brown and then to an off-white color. The mixture was diluted with 4.8 L of dichloromethane and then washed (12 L separatory flask) with 7×2 L of 0.25M potassium carbonate. Salt was added to some washes to improve phase separation. After 2 additional 2 L washes with water, the organic phase was coagulated in 10 parts of isopropanol. The precipitate, a fine yellow powder, was collected and dried at ~60° C. under vacuum. The dried product (238 g) had a melting point of about 246° C. The proton NMR was consistent with the expected structure. LC analysis showed one major product with two minor impurities.

EXAMPLE 2

Determination of Bis-Maleimide and Maleimide-Isomaleimide Content in Examples 1 and A The crude bismaleimide product mixture of Example 1 was further analyzed by LC chromatography, by NMR and by IR methods. The product mixture was found to comprise >90 wt. % Bis-maleimide, while approximately 5 wt. % was α-(4-maleimidophenyl)-α'-(4-isomaleimidophenyl)-meta-diisopropylbenzene, identified by comparison with an authentic sample.

Analysis of the product mixture of comparative Example A by the same techniques found >95% bismaleimide and no detectable level of any isomaleimide compound.

EXAMPLE 3

Preparation and Isolation of the Maleimide-Isomaleimide

The synthesis of crude maleimide-isomaleimide was carried out using substantially the procedures and materials of Example 1; however, no heat was applied, either to the initial reaction mixture or during the dehydration step. During the dehydrating step the reaction mixture first formed a clear sllution, then became opaque due to the presence of precipitated solids. Stirring was continued and the reaction progress was followed by liquid chromatography. After approximately 4 days at room temperature, the reaction mixture comprised maleimide-isomaleimide and bis-isomaleimide in an 85/15 ratio. A portion of the resulting slurry was added to 5 to 10 volumes of water in a rapidly-stirring blender. The solid product, collected by filtration, was washed with 0.25M aqueous potassium carbonate and with water, then dried. According to LC analysis, the product mixture comprised mainly (82%) α'-(4-maleimidophenyl)-α'-(4-isomaleimido-phenyl)-meta-di-isopropyl benzene, together with the corresponding bis-isomaleimide (8%), the bis-maleimide (6%), and 4% minor impurities. A second portion of the slurry was filtered directly, giving a solid that when washed and dried as before, consisted of a 90/10 ratio of the imideisoimide and the corresponding bis-isomaleimide.

The results of LC analysis of the crude product mixture produced in Examples 1 and 3 demonstrate that the amounts of the bismaleimide, bis-isomaleimide and maleimide-isomaleimide compound produced will greatly vary, depending upon reaction times and temperatures. The inoolubility of the novel imide-isoimide product in the reaction medium relative to that of the bis-imide product is advantageous in that conversion of the solid to the bis-imide appears to be very slow, and permits isolation of the desired product.

However, during the preparation of ten other bis-maleimides, following the procedure of Example 1 but using a variety of different diamines, no other instance of a slurry reforming during the dehydration stage was noted. This includes the preparation of the para-para compound described in Control Example A. The insolubility of the maleimide-isomaleimide compound of this invention, as set forth in Example 3, is thus completely unexpected and could not have been predicted from consideration of any disclosure of the prior art, or by one skilled in this art.

It will be apparent that the production and isolation of the maleimide-isomaleimide compound of this invention as a stable compound is thus completely surprising and unexpected.

EXAMPLE 4

Preparation of Bismaleimide/Coreactant Casting

A mixture of 6.2 g of the product of Example 1 and 3.8 g of o, o'-diallylbisphenol A was blended in a 25 ml flask on a rotary evaporator at 125° C. for 10 minutes to form a transparent gold solution. This was poured into a small casting frame (~4"×441 glass plates with a 1/16" Teflon spacer frame) and cured with the following schedule.

The casting was cured by heating from 25° C. to 79° C. at 1.5° C./min.; holding at 79° C. for 2 hours; heating from 79° C. to 177° C. at 1.5° C./min.; holding at 177° C. for 4 hours, heating to 246° C. at 1° C./min.; holding at 246° C. for 4 hours; and then cooling to room temperature at 1.5° C./min. Other cure schedules could also be used having shorter or longer hold periods at these or other temperatures.

The transparent, dark gold casting was cut into DMA (dynamic mechanical analysis) test specimens which showed a Tg of 237° C. when tested at a heating rate of 5°/minute. After soaking in water at 160° F. for two weeks, the casting samples absorbed 2.2% water.

The invention will thus be seen to be a novel maleimide-isomalemide compound as a composition of matter, and a method for its preparation. The compound of this invention has particular utility as a synthesis intermediate, because of the corresponding unequal reactivity of the two functional groups.

We claim:

1. The maleimide-isomaleimide compound of the following structural formula:

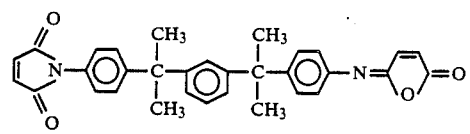

2. A composition comprising alpha-4-maleimidophenyl)-alpha-(4-isomaleimidophenyl)-meta-diisopropyl benzene prepared by the process comprising the steps of:
   (a) stirring a mixture comprising a solvent, maleic anhydride and 2,2-bis(4-aminophenyl)-meta-diisopropyl benzene to form the corresponding bis-(maleamic-acid); and
   (b) cyclizing the said bis-(maleimide-acid) by dehydration in the presence of an aliphatic acid anhydride.

* * * * *